(12) United States Patent
Makino

(10) Patent No.: US 11,612,310 B2
(45) Date of Patent: Mar. 28, 2023

(54) ENDOSCOPE SYSTEM

(71) Applicant: HOYA CORPORATION, Tokyo (JP)

(72) Inventor: Takao Makino, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 335 days.

(21) Appl. No.: 17/260,801

(22) PCT Filed: Mar. 20, 2019

(86) PCT No.: PCT/JP2019/011922
§ 371 (c)(1),
(2) Date: Jan. 15, 2021

(87) PCT Pub. No.: WO2020/188825
PCT Pub. Date: Sep. 24, 2020

(65) Prior Publication Data
US 2021/0279498 A1   Sep. 9, 2021

(51) Int. Cl.
| | |
|---|---|
| A61B 1/045 | (2006.01) |
| G06T 7/90 | (2017.01) |
| A61B 1/00 | (2006.01) |
| A61B 5/02 | (2006.01) |
| G06V 10/56 | (2022.01) |
| G06V 10/75 | (2022.01) |

(Continued)

(52) U.S. Cl.
CPC .......... *A61B 1/045* (2013.01); *A61B 1/00045* (2013.01); *A61B 1/000094* (2022.02);
(Continued)

(58) Field of Classification Search
CPC .............. A61B 1/045; A61B 1/000094; A61B 1/00045; A61B 5/02042; A61B 1/05;
(Continued)

(56) References Cited

U.S. PATENT DOCUMENTS 9,186,051 B2 * 11/2015 Hirota ................. G06V 10/462
2012/0051640 A1   3/2012 Kanda et al.
(Continued)

FOREIGN PATENT DOCUMENTS

| | | |
|---|---|---|
| JP | 2012-45056 | 3/2012 |
| JP | 2013-111420 | 6/2013 |

(Continued)

OTHER PUBLICATIONS

Official Communication issued in International Bureau of WIPO Patent Application No. PCT/JP2019/011922, dated Jun. 11, 2019.
(Continued)

*Primary Examiner* — Ali Bayat
(74) *Attorney, Agent, or Firm* — Greenblum & Bernstein, P.L.C.

(57) ABSTRACT

An electronic endoscope system includes an image processing unit that uses a numerical value to evaluate an appearance feature appearing in a biological tissue by using an images captured by an electronic endoscope. The image processing unit calculates a first pixel evaluation value indicating a degree of a first feature, which is featured by a first color component or a first shape appearing in an attention area in the biological tissue, and which relates to the first color component or the first shape, for each pixel from the image, and calculates a first representative evaluation value relating to the first feature by integrating the first pixel evaluation value. Furthermore, the image processing unit evaluates a degree of a second feature that shares the first color component or the first shape with the first feature.

7 Claims, 11 Drawing Sheets

(51) Int. Cl.
*G06V 10/25* (2022.01)
*G06V 10/141* (2022.01)
*G06V 10/46* (2022.01)

(52) U.S. Cl.
CPC ............ *A61B 5/02042* (2013.01); *G06T 7/90* (2017.01); *G06V 10/141* (2022.01); *G06V 10/25* (2022.01); *G06V 10/46* (2022.01); *G06V 10/56* (2022.01); *G06V 10/758* (2022.01); *G06T 2207/10024* (2013.01); *G06T 2207/10068* (2013.01); *G06T 2207/30096* (2013.01); *G06T 2207/30101* (2013.01)

(58) Field of Classification Search
CPC ....... A61B 5/0084; A61B 5/447; A61B 5/489; G06T 7/90; G06T 2207/10024; G06T 2207/10068; G06T 2207/30096; G06T 2207/30101; G06T 2207/20021; G06T 2207/20024; G06T 7/0012; G06V 10/141; G06V 10/25; G06V 10/46; G06V 10/56; G06V 10/758; G06V 2201/031
USPC ........................................................ 382/128
See application file for complete search history.

(56) References Cited

U.S. PATENT DOCUMENTS

| | | |
|---|---|---|
| 2013/0051641 A1 | 2/2013 | Tanaka et al. |
| 2014/0270377 A1 | 9/2014 | Kanda et al. |
| 2014/0333654 A1* | 11/2014 | Li .................. G06T 11/001 345/591 |
| 2014/0340497 A1 | 11/2014 | Shigeta |
| 2015/0356369 A1 | 12/2015 | Kitamura et al. |
| 2016/0173734 A1* | 6/2016 | Ikenaga ............ G01J 3/4406 382/133 |
| 2018/0279866 A1 | 10/2018 | Makino |
| 2019/0192048 A1 | 6/2019 | Makino et al. |
| 2019/0374093 A1* | 12/2019 | Endo ................ A61B 1/045 |
| 2020/0364866 A1 | 11/2020 | Makino |
| 2020/0375439 A1* | 12/2020 | Endo ................ A61B 1/3137 |

FOREIGN PATENT DOCUMENTS

| | | |
|---|---|---|
| JP | 2014-221168 | 11/2014 |
| JP | 2016-067706 | 5/2016 |
| JP | 6912608 | 8/2021 |
| WO | 2012/114600 | 8/2012 |
| WO | 2014/132694 | 9/2014 |
| WO | 2017/057680 | 4/2017 |
| WO | 2018/043550 | 3/2018 |

OTHER PUBLICATIONS

Sep. 7, 2021 Japanese Office Action issued in corresponding Japanese Patent Application No. 2021-506120 and English translation thereof.

* cited by examiner

ENDOSCOPE SYSTEM

TECHNICAL FIELD

The present invention relates to an endoscope system that performs image processing on an image of a biological tissue.

BACKGROUND ART

In a lesion area in a biological tissue, various levels of severity are present from an inflammation indicating a red color due to a thinned and roughened mucosal layer of the biological tissue to an ulcer in which the mucosal layer and a lower layer thereof are partially lost. For example, an ulcer area of a lesion of an ulcerative colitis (UC) shows a white color including fur or mucopus, and an inflamed area shows a red color including edema or hemorrhagic. The lesion area can be imaged and observed with an endoscope system.

However, in order for an operator to be able to identify a normal area and the lesion area by using a difference in colors included in an image obtained by an endoscope, it is necessary to receive a long-term training under a guidance of an expert. In addition, it is not easy for even a skilled operator to identify the lesion area by using a slight color difference, and careful work needs to be carried out. Therefore, it is preferable that the endoscope system provides an evaluation result obtained by objectively converting a degree of the lesion in the lesion area into a numerical value.

In contrast, an endoscope system is known which can stably calculate an evaluation value by suppressing fluctuations in the evaluation value of the inflamed area which are caused by brightness of the image, and can suppress a processing load in calculating the evaluation value (Patent Literature 1).

CITATION LIST

Patent Literature

Patent Literature 1: International Publication No. 2017/057680

SUMMARY OF INVENTION

Technical Problem

The above-described endoscope system includes a light source device that irradiates an object with illumination light, an image acquisition unit that captures an image by causing an image sensor to receive reflected light from the object, and acquires a color image including at least three or more color components, and an evaluation unit that obtains an evaluation result relating to a target disease of each pixel, based on an angle formed between a line segment connecting a predetermined reference point set within a color plane and a pixel correspondence point within the color plane of each pixel forming the color image acquired by the image acquisition unit and a reference axis having a correlation with a target disease, within the color plane defined by at least two color components out of at least three or more color components. The reference axis is set to pass through a predetermined reference point. The reference axis is at least one of an axis having a correlation with a target disease in which an inflamed degree within the color plane has a predetermined value or smaller and an axis having a correlation with a target disease in which an inflamed degree has a predetermined value or greater within the color plane.

According to this configuration, an inflammation evaluation value can be stably calculated by suppressing fluctuations in the inflammation evaluation value which are caused by the brightness of the image, and a processing load in calculating the inflammation evaluation value can be suppressed.

According to the above-described endoscope system, a degree of the target disease relating to the color component can be evaluated. For example, when the target disease is an inflammation, in the vicinity of the inflamed area showing a red color due to a thinned mucosal layer, there exist a blood vessel area showing the red color and a region showing the red color, a surface of which is covered with blood after bleeding since a mucous membrane disappears due to the inflammation. Therefore, there is a disadvantage in that the inflammation evaluation value evaluated as the inflamed area includes an evaluation of the blood vessel area or the region covered with the blood. Therefore, in some cases, it may be difficult to accurately evaluate a degree of the inflammation by using the above-described inflammation evaluation value.

In addition, a degree of red chromaticity of the blood vessel which appears in the vicinity of the inflamed area showing the red color and the ulcer area showing a white color varies depending on a degree of the inflammation and a degree of the ulcer. Accordingly, it is preferable to evaluate a degree of the lesion including the inflammation and the ulcer, together with an evaluation result of a degree of a red color component of the blood vessel. In this case, the blood vessel area has a linear shape. Accordingly, it is possible to detect the blood vessel area by performing linear pattern matching. However, in many cases, a plurality of inflammations and ulcers exist in the vicinity of the blood vessel in the lesion area. For example, in some cases, the inflamed area interposed between two ulcers may form a band shape. In this case, there is a disadvantage in that an elongated and strip-shaped portion interposed between the two ulcers in addition to the blood vessel area is erroneously detected by performing the linear pattern matching. Therefore, in some cases, it may be difficult to accurately evaluate a degree of the lesion.

Therefore, the present invention aims to provide an endoscope system which can use a numerical value to accurately evaluate an appearance feature appearing in an attention area of a biological tissue, for example, such as a lesion area, for example, certainty of a blood vessel, and a degree of a red color component caused by an inflammation.

Solution to Problem

An aspect of the present invention is an endoscope system. The endoscope system includes an electronic endoscope configured to image a biological tissue, a processor including an image processing unit configured to use a numerical value to evaluate a degree of an appearance feature appearing in an attention area of the biological tissue by using an image of the attention area of the biological tissue imaged by the electronic endoscope, and a monitor configured to display information on the numerical value.

The image processing unit includes a feature amount calculation unit configured to calculate a first pixel evaluation value featured by a first color component or a first shape appearing as a first feature in the attention area, the first pixel evaluation value indicating a degree of the first feature which relates to the first color component or the first shape indicated by the attention area, for each pixel from the image, a representative value calculation unit configured to calculate a first representative evaluation value relating to the first feature of the imaged biological tissue by integrating the first pixel evaluation value of each pixel in the image, and a representative value adjustment unit configured to evaluate a degree of a second feature that shares the first color component or the first shape with the first feature and that appears in the attention area of the biological tissue which affects a level of the first pixel evaluation value by using at least one of a second color component and a second shape of the attention area, and to increase or decrease the first representative evaluation value, based on an evaluation result of a degree of the second feature.

It is preferable that the representative value adjustment unit is configured to evaluate a degree of a third feature that shares the first color component or the first shape with the first feature and that appears in the attention area which affects a level of the first pixel evaluation value by using at least one of a third color component and a third shape of the attention area, and to increase or decrease the first representative evaluation value, based on an evaluation result of a degree of the second feature and an evaluation result of a degree of the third feature.

It is preferable that the first pixel evaluation value is a value obtained by converting a degree of certainty relating to the first shape into a numerical value, as a degree of the first feature, and the evaluation result of a degree of the second feature is an evaluation result relating to the second color component in the image.

It is preferable that a degree of the first feature is certainty of a linearly extending blood vessel in a blood vessel appearing on a surface of the biological tissue, a degree of the second feature is a degree of an ulcer of the biological tissue, and the representative value adjustment unit is configured to evaluate the degree of the second feature by using at least one of a parameter of a distribution spread in a histogram distribution relating to values obtained by converting a red color component for each pixel of the image into a numerical value, and a maximum value out of the values obtained by converting the red color component into the numerical value.

It is preferable that the first pixel evaluation value is a value obtained by converting a degree of the first color component into a numerical value as a degree of the first feature, the evaluation result of a degree of the second feature is an evaluation result of a degree including the second color component in a region where an appearing range of the second feature is extracted as the second shape, and the second color component and the first color component are the same pixel color components which determine a pixel value of the image.

It is preferable that a degree of the first feature is a degree of an inflammation of an inflamed area in the attention area, and the degree of inflammation is evaluated by a degree of a red color component of the image, and a degree of the second feature is a degree of bleeding in a region where a surface of the biological tissue is covered with blood due to bleeding of the biological tissue, and the degree of the bleeding is a value obtained by converting a degree including the red color component in the region into a numerical value.

It is preferable that the image processing unit is configured to obtain severity of a lesion in which a degree of the lesion of the biological tissue is expressed as one value by using at least information on a color component of the image, from the image of the biological tissue which is obtained by the electronic endoscope, the feature amount calculation unit is configured to calculate a plurality of pixel evaluation values corresponding to a plurality of appearance features, in which each of the plurality of appearance features appearing in the lesion area is featured by a color component indicated by the lesion area or a shape of the lesion area, the plurality of pixel evaluation values indicating each degree of the plurality of features relating to the color component indicated by the lesion area or the shape of the lesion area, for each pixel from the image, the plurality of pixel evaluation values include the first pixel evaluation value, the representative value calculation unit is configured to calculate the plurality of representative evaluation values including the first representative evaluation value of the biological tissue imaged by integrating each of the plurality of pixel evaluation values including the first pixel evaluation value of each pixel in the image for each of the plurality of appearance features, and the image processing unit includes an integration unit configured to calculate one numerical value obtained by calculating and integrating at least two representative evaluation values including the first representative evaluation value adjusted by the representative value adjustment unit out of the plurality of representative evaluation values as severity of the lesion.

Advantageous Effects of Invention

According to the above-described endoscope system, it is possible to use a numerical value to accurately evaluate the appearance feature appearing in the attention area of the biological tissue, for example, certainty of the blood vessel, and a degree of the red color component caused by the inflammation.

DESCRIPTION OF EMBODIMENTS

Brief Description of Embodiment

Figure 1:
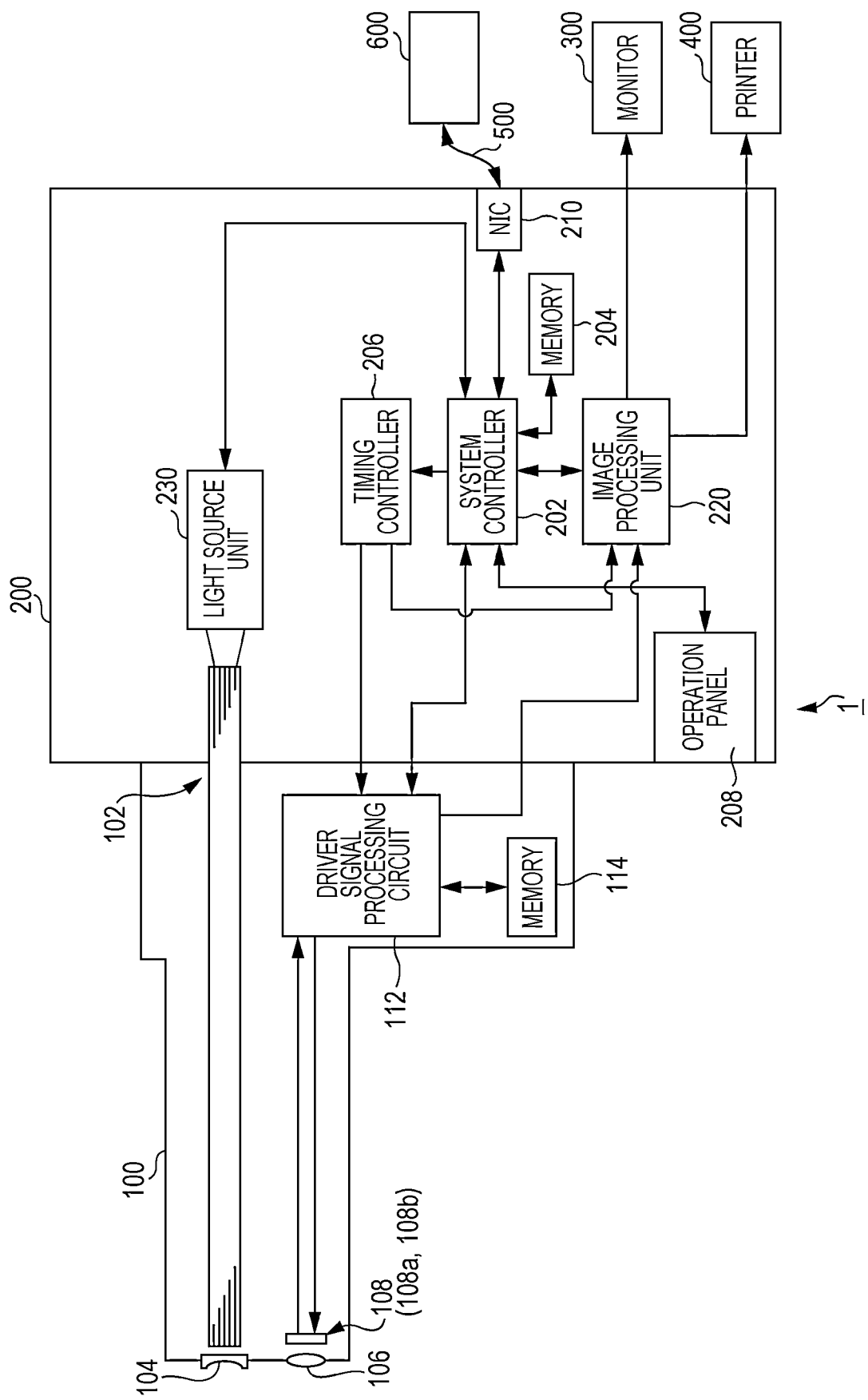
FIG. 1 is a block diagram illustrating an example of a configuration of an endoscope system according to an embodiment.

Hereinafter, an embodiment of an endoscope system will be described in detail.

When a degree of an appearance feature appearing in an attention area such as a lesion area of a biological tissue is evaluated by using a numerical value, the endoscope system can use the numerical value to express a degree of a feature relating to a color component or a shape appearing in the attention area. However, in some cases, the color component or the shape may overlap another appearance feature appearing in the biological tissue. That is, in some cases, an evaluation result obtained by using the numerical value to express a degree of the feature relating to the color component or the shape appearing in the attention area may overlap an evaluation result obtained by another feature.

Therefore, an image processing unit according to the embodiment configured to use a numerical value to evaluate an appearance feature appearing in the attention area of the biological tissue by using an image captured by an electronic endoscope includes a feature amount calculation unit, a representative value calculation unit, and a representative value adjustment unit. In this manner, an evaluation result in which a degree of the feature relating to the color component or the shape appearing in the attention area is expressed by the numerical value is adjusted, based on an evaluation result of another overlapping feature relating to the color component or the shape.

The attention area is not limited to the lesion area, and may be a normal area. For example, the attention area may be a normal area that does not lead to a lesion, such as an area showing a feature in which many blood vessels appear on a surface of the biological tissue as a pre-lesion sign.

That is, the feature amount calculation unit of the image processing unit according to the present embodiment is configured to calculate a first pixel evaluation value featured by a first color component or a first shape appearing as a first feature in the attention area, for each pixel from the image. The first pixel evaluation value is an evaluation value indicating a degree of the first feature which relates to the first color component or the first shape indicated by the attention area.

The representative value calculation unit is configured to calculate a first representative evaluation value relating to the first feature of the biological tissue imaged by integrating the first pixel evaluation value of each pixel calculated by the feature amount calculation unit.

The representative value adjustment unit is configured to evaluate a degree of a second feature different from the first feature by using at least one of a second color component of the attention area and a second shape of the attention area, and to increase or decrease the first representative evaluation value, based on an evaluation result of a degree of the second feature. The second feature is an appearance feature that shares the first color component or the first shape with the first feature and that appears in the biological tissue which affects a level of the first pixel evaluation value. Adjustment of the first representative evaluation value includes not only adjustment for decreasing the first representative evaluation value, but also adjustment for increasing the first representative evaluation value, since there is a case where the first representative evaluation value may be decreased as a degree of the second feature is stronger.

In this way, the image processing unit calculates the first representative evaluation value obtained by integrating a degree of the first feature with the pixel evaluation value for each image which relates to the first color component or the first shape. Thereafter, the image processing unit removes influence of the second feature included in the first representative evaluation value, based on the evaluation result in which the degree of the second feature that shares the first color component or the first shape with the first feature is evaluated by using the second color component or the second shape. In this manner, the image processing unit obtains the adjusted first representative evaluation value in which the first representative evaluation value is increased or decreased. For example, the second color component or the second shape is different from the first color component or the first shape.

The image processing unit removes the influence of the second feature included in the first representative evaluation value. Accordingly, it is possible to use the numerical value to accurately evaluate the appearance feature appearing in the attention area of the biological tissue, for example, certainty of the blood vessel, and the degree of the red color component which is caused by inflammation.

Here, when the first feature is the certainty of the blood vessel, for example, the numerical value is used to evaluate the degree of the certainty of the blood vessel by using a linear pattern that approximates a blood vessel shape. In this case, the second feature includes an ulcer. A degree of the blood vessel which appears as an image on a surface of the biological tissue varies depending on a degree of the inflammation. When the certainty of the blood vessel is evaluated as the degree of the first feature, the feature amount calculation unit converts the certainty of the blood vessel (blood vessel shape) into the numerical value by using a matching degree with the linear pattern, and obtains the pixel evaluation value of the certainty of the blood vessel for each pixel. The representative value calculation unit obtains the first feature, that is, the representative evaluation value of the certainty of the blood vessel by integrating the obtained pixel evaluation value. In the evaluation result, a strip-shaped and elongated inflamed area interposed between two ulcer areas affects the evaluation result of the certainty of the blood vessel. However, in this case, there exist a white region of the two ulcer areas and a red region of the inflamed area interposed between the two ulcer areas. As the degree of the ulcer becomes stronger, a degree of the red color component of the inflamed area interposed between the two ulcer areas becomes stronger. Therefore, the representative value adjustment unit evaluates a distribution of the red color component in the image, and adjusts the numerical value to increase a decreasing amount of the numerical value of the evaluation result of the certainty of the blood vessel, as the degree of the red color component becomes higher. In this manner, the representative value adjustment unit increases or decreases the representative evaluation value evaluated by using the certainty of the blood vessel, based on the evaluation result (evaluation result of the second feature) obtained by evaluating the degree of the red color component.

In addition, when the first feature is the inflammation of the inflamed area and the degree of the red color component appearing in the inflamed area is evaluated by using the numerical value, the second feature includes a degree of bleeding. The feature amount calculation unit obtains an evaluation value obtained by converting the degree of the red color component appearing at the inflamed area into the numerical value for each pixel, and the representative value calculation unit integrates the obtained evaluation values to obtain the representative evaluation value of the first feature. The evaluation result also includes the evaluation result of a bleeding area. The bleeding area is an area where the blood bleeds and covers the surface of the biological tissue, and a boundary with an area not covered with the blood appears as an edge. Therefore, the representative value adjustment unit extracts the bleeding area by using a known edge detection technique. Furthermore, the representative value adjustment unit obtains the evaluation result in which the degree of the red color component of the extracted bleeding area is converted into the numerical value. In this manner, the representative value adjustment unit increases or decreases the representative evaluation value obtained by evaluating the degree of the red color component as the first feature, based on the evaluation result in which the degree of the red color component of the bleeding area is converted into the numerical value. In this case, the evaluation result of the degree of the second feature is the evaluation result of the degree including the red color component (second color component) in a region where an appearing range of the bleeding (second feature) is extracted as the second shape, and the red color component (second color component) and the red color component (first color component) used as the inflamed area are the same pixel color components which determine the pixel value of the image.

When a surface model appearing on the biological tissue is the first feature, the feature amount calculation unit evaluates a degree of the surface model. For example, as the degree of the surface model, a pixel having a greater pixel value of the surface model can be detected by using a simultaneous occurrence matrix which is a known texture analysis technique. The representative value calculation unit integrates the pixel values of the obtained pixels to obtain the representative evaluation value of the first feature. At this time, the representative evaluation value also includes the evaluation result of the blood vessel shape. Therefore, the representative value adjustment unit obtains the certainty of the blood vessel in which the certainty of the blood vessel is converted into the numerical value and integrated for each pixel by using the matching degree with the linear pattern, as the evaluation result of the second feature. In this manner, the representative value adjustment unit increases or decreases the representative evaluation value obtained by evaluating the degree of the surface model as the first feature, based on the evaluation result of the second feature.

In this way, the first feature and the second feature include the inflammation, the ulcer, the certainty of the blood vessel, and the surface model. However, as the first feature or the second feature, a residue remaining on a surface of a biological substance can also be used as a target. For example, the residue is a residue of food remaining in intestines without being discharged from the intestines. The residue has a relatively strong green color component or blue color component, compared to the biological tissue, and a ratio of the color components to the red color component is high. Therefore, the ratio can be used to detect an image of the residue appearing in the image. A region of the residue in the image can be extracted by using a known edge detection technique in a ratio image in which the ratio of the green color component or the blue color component is set as the pixel value.

The endoscope system disclosed herein increases or decreases the evaluation result of the first feature, based on the evaluation result in which the second feature that shares the first color component or the first shape serving as an index of the first feature with the first feature is evaluated by using the second color component or the second shape as an index. However, in addition to the second feature, the evaluation result of the first feature may be adjusted, based on the evaluation result in which a third feature that shares the first color component or the first shape serving as the index of the first feature with the first feature is further evaluated by using a third color component or a third shape as an index. For example, the third color component or the third shape is different from the first color component or the first shape.

When the first feature is the certainty of the blood vessel, as described above, the strip-shaped and elongated inflamed area interposed between the two ulcer areas also contributes to the evaluation result of the certainty of the blood vessel. However, in some cases, surface irregularities of the biological tissue may also contribute to the evaluation result of the certainty of the blood vessel. That is, the surface irregularities can be the third feature. With regard to the surface irregularities, the surface irregularities are converted into the numerical value as the evaluation result of the third feature, based on a standard deviation obtained by statistically processing the evaluation values obtained by evaluating a degree of a predetermined color component, for example, the red color component for each pixel. As the degree of surface irregularities becomes stronger, the above-described standard deviation becomes greater. Therefore, the value converted into the numerical value based on this standard deviation is used as the evaluation result of the third feature, and the certainty of the blood vessel is increased or decreased, based on this evaluation result. In this manner, it is possible to remove the influence of the surface irregularities that contribute to the certainty of the blood vessel.

That is, the representative evaluation value indicating the degree of the certainty of the blood vessel which is the first feature can be increased or decreased, based on the evaluation result (evaluation result of the second feature) obtained by evaluating the degree of the red color component and the evaluation result (evaluation result of the third feature) of the surface irregularities.

(Specific Description of Embodiment)

FIG. 1 is a block diagram illustrating a configuration of an electronic endoscope system 1 according to an embodiment of the present embodiment. As illustrated in FIG. 1, the electronic endoscope system 1 includes an electronic scope (electronic endoscope) 100, processor for an electronic endoscope 200, a monitor 300, and a printer 400.

The processor for the electronic endoscope 200 includes a system controller 202 and a timing controller 206. The system controller 202 executes various programs stored in the memory 204, and integrally controls the whole electronic endoscope system 1. In addition, the system controller 202 changes various settings of the electronic endoscope system 1 in accordance with an instruction of a user (operator or assistant) which is input to an operation panel 208. The timing controller 206 outputs a clock pulse for adjusting an operation timing of each unit to each circuit in the electronic endoscope system 1.

The processor for the electronic endoscope 200 includes a light source unit 230 that supplies illumination light to the electronic scope 100. Although not illustrated, for example, the light source unit 230 includes a high intensity lamp that emits white illumination light by receiving drive power supply from a lamp power source, for example, such as a xenon lamp, a metal halide lamp, a mercury lamp, or a halogen lamp. The light source unit 230 is configured so that the illumination light emitted from the high intensity lamp is collected by a condensing lens (not illustrated), and thereafter, is incident on an incident end of a light carrying bundle (LCB) 102 which is a bundle of optical fibers of the electronic scope 100 via a dimmer (not illustrated).

Alternatively, the light source unit 230 includes a plurality of light emitting diodes that emit light in a wavelength band of a predetermined color. The light source unit 230 is configured so that the light emitted from the light emitting diode is synthesized by using an optical element such as a dichroic mirror, and the synthesized light is collected as illumination light by a condensing lens (not illustrated), and thereafter, is incident on the incident end of the light carrying bundle (LCB) 102 of the electronic scope 100. A laser diode can be used instead of the light emitting diode. The light emitting diode and the laser diode have features such as low power consumption and a low heat generation amount, compared to other light sources. Therefore, there is an advantage in that a bright image can be acquired while suppressing the power consumption and the heat generation amount. Since the bright image can be acquired, accuracy in evaluating the lesion can be improved.

In an example illustrated in FIG. 1, the light source unit 230 is provided by being incorporated in the processor for the electronic endoscope 200, but may be provided in the electronic endoscope system 1 as a device separate from the processor for the electronic endoscope 200. In addition, the light source unit 230 may be provided in a distal tip of the electronic scope 100 (to be described later). In this case, the LCB 102 that guides the illumination light is unnecessary.

The illumination light incident into the LCB 102 from the incident end propagates into the LCB 102, and is emitted from the incident end of the LCB 102 disposed inside the distal tip of the electronic scope 100, and illuminates the biological tissue serving as an object via a light distribution lens 104. The reflected light from the object forms an optical image on a light receiving surface of an image sensor 108 via an objective lens 106.

For example, the image sensor 108 is a single-plate color charge-coupled device (CCD) image sensor in which various filters of an infra red (IR) cut filter 108a and a Bayer array color filter 108b are disposed on a light receiving surface, and generates each primary color signal of R (red), G (green), and B (blue) according to an optical image formed on the light receiving surface. Instead of the single-plate color CCD image sensor, a single-plate color complementary metal oxide semiconductor (CMOS) image sensor can also be used. In this way, the electronic scope 100 uses the image sensor 108 to image the biological tissue inside a body cavity.

A driver signal processing circuit 112 and a memory 114 are provided inside a connector unit connected to the processor for the electronic endoscope 200 in the electronic scope 100. The driver signal processing circuit 112 generates an image signal (brightness signal Y, color difference signal Cb and Cr) by performing predetermined signal processing such as color interpolation and matrix calculation on the primary color signal input from the image sensor 108, and outputs the generated image signal to an image processing unit 220 of the processor for the electronic endoscope 200. In addition, the driver signal processing circuit 112 accesses the memory 114, and reads specific information of the electronic scope 100. For example, the specific information of the electronic scope 100 recorded in the memory 114 includes the number of pixels or sensitivity of the image sensor 108, a frame rate with which the electronic scope 100 is operable, and a model number. The driver signal processing circuit 112 outputs the specific information read from the memory 114 to the system controller 202.

The system controller 202 performs various calculations, based on the specific information of the electronic scope 100, and generates a control signal. The system controller 202 controls an operation and a timing of each circuit inside the processor for the electronic endoscope 200 by using the generated control signal so that processing suitable for the electronic scope 100 connected to the processor for the electronic endoscope 200 is performed.

The timing controller 206 supplies a clock pulse to the driver signal processing circuit 112, the image processing unit 220, and the light source unit 230 in accordance with timing control of the system controller 202. The driver signal processing circuit 112 performs driving control on the image sensor 108 at a timing synchronized with a frame rate of a video image processed on the processor for the electronic endoscope 200 side in accordance with the clock pulse supplied from the timing controller 206.

Under the control of the system controller 202, the image processing unit 220 generates a video signal for displaying an endoscope image on a monitor, based on the image signal input from the driver signal processing circuit 112, and outputs the video signal to the monitor 300. Furthermore, the image processing unit 220 uses a numerical value to evaluate a degree of an appearance feature appearing in an attention area from an image of the attention area of the biological tissue which is obtained by the electronic scope 100. In addition, the image processing unit 220 generates a color map image in which colors are replaced, based on an evaluation result obtained by using the numerical value to evaluate the degree of the appearance feature. The image processing unit 220 generates a video signal for displaying information on the evaluation result and the color map image on the monitor, and outputs the video signal to the monitor 300. In this manner, an operator can receive the evaluation result relating to the feature of the attention area of the biological tissue through the image displayed on a display screen of the monitor 300. When necessary, the image processing unit 220 outputs the color map image and the information on the evaluation result to the printer 400.

The processor for the electronic endoscope 200 is connected to a server 600 via a network interface card (NIC) 210 and a network 500. The processor for the electronic endoscope 200 can download information relating to an endoscopic examination (for example, patient's electronic medical record information or operator information) from the server 600. For example, the downloaded information is displayed on the display screen of the monitor 300 or the operation panel 208. In addition, the processor for the electronic endoscope 200 uploads an endoscopic examination result (endoscope image data, an examination condition, an image analysis result, or an operator's opinion) to the server 600. In this manner, it is possible to store the endoscopic examination result in the server 600.

Figure 2:
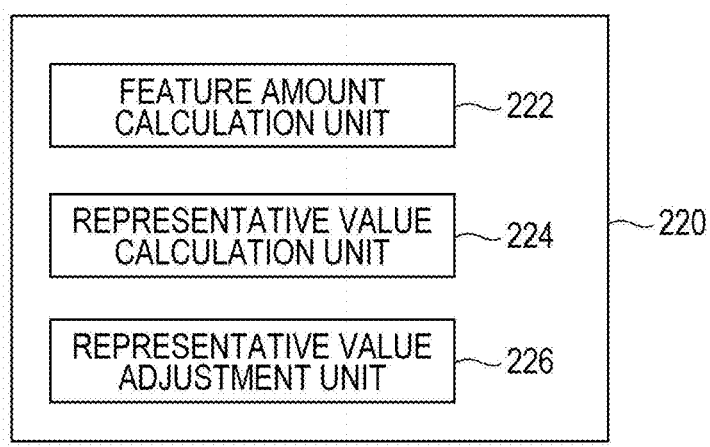
FIG. 2 is a view illustrating an example of a configuration of an image processing unit of the endoscope system according to the embodiment.

FIG. 2 is a view for describing an example of a configuration of the image processing unit 220. The image processing unit 220 is configured to use a numerical value to evaluate a degree of the appearance feature appearing in the attention area of the biological tissue by using an image of the attention area of the biological tissue. The image processing unit 220 includes a feature amount calculation unit 222, a representative value calculation unit 224, and a representative value adjustment unit 226.

Hereinafter, as an example, an operation of the image processing unit 220 will be described with reference to a case where the first feature is the certainty of the blood vessel and the second feature is the ulcer.

The feature amount calculation unit 222 evaluates the degree of the certainty of the blood vessel which is the first feature. Specifically, the feature amount calculation unit 222 is configured to calculate a pixel evaluation value (first pixel evaluation value) featured by a line shape (first shape) appearing in the attention area. The pixel evaluation value is a value indicating the certainty of the blood vessel which relates to the line shape indicated by the attention area, and this pixel evaluation value is configured to be calculated for each pixel from the image.

Figure 3:
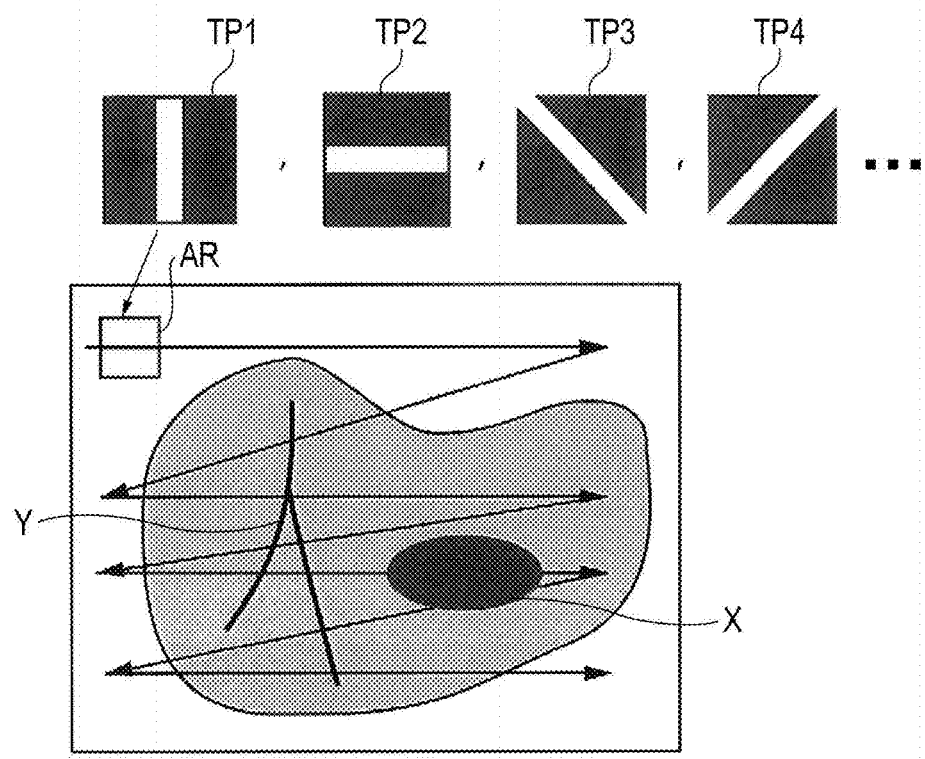
FIG. 3 is a view illustrating a method in which a feature amount calculation unit included in the image processing unit illustrated in FIG. 2 evaluates certainty of a blood vessel.

FIG. 3 is a view for describing a method in which the feature amount calculation unit 222 evaluates the certainty of the blood vessel.

As illustrated in FIG. 3, the feature amount calculation unit 222 obtains a matching degree indicating a degree of correlation between a shape of an examination target area AR of a portion of the image of the biological tissue and a line shape of each of a plurality of templates TP1 to TP4. In the matching degrees corresponding to the plurality of respective templates TP1 to TP4, a highest matching degree is set as a value of the certainty of the blood vessel in the examination target area AR. The value of the certainty of the blood vessel is assigned to a pixel located in the center of the examination target area AR as a pixel evaluation value. The templates TP1 to TP4 are configured to include pixels, and the templates TP1 to TP4 have a plurality of line shapes having mutually different extending directions. In the templates TP1 to TP4, each pixel has a pixel value in accordance with each line shape. As illustrated in FIG. 3, the examination target areas AR are moved sequentially from an end of the image along an arrow while overlapping each other. In this manner, the degree of correlation between the pixel value of the image inside the examination target area AR and the value of the pixel corresponding to each of the templates TP1 to TP4 is obtained. According to the embodiment, the templates TP1 to TP4 have four line shapes extending in four different extending directions as shapes featured by the blood vessel. When the examination target area AR includes a blood vessel region, the pixel value inside the examination target area AR includes information on a feature shape such as the blood vessel extending in a stripe shape. Accordingly, the certainty of the blood vessel can be calculated. The templates TP1 to TP4 have a value for each pixel corresponding to a white region and a black region which illustrated in FIG. 3. Therefore, according to the embodiment, the matching degree is a correlation coefficient between the pixel value of the templates TP1 to TP4 and the corresponding pixel evaluation value of the examination target area AR. In addition, according to the embodiment, the matching degree may be a total value obtained by multiplying each of filter coefficients by an image value of the corresponding pixel of the examination target area AR, by using the value for each pixel of the templates TP1 to TP4 as the filter coefficients of a spatial filter.

The highest matching degree having the greatest value in the matching degrees calculated for the respective templates TP1 to TP4 is assigned to a central pixel of the examination target area AR, as the value indicating the certainty of the blood vessel region.

Figure 4:
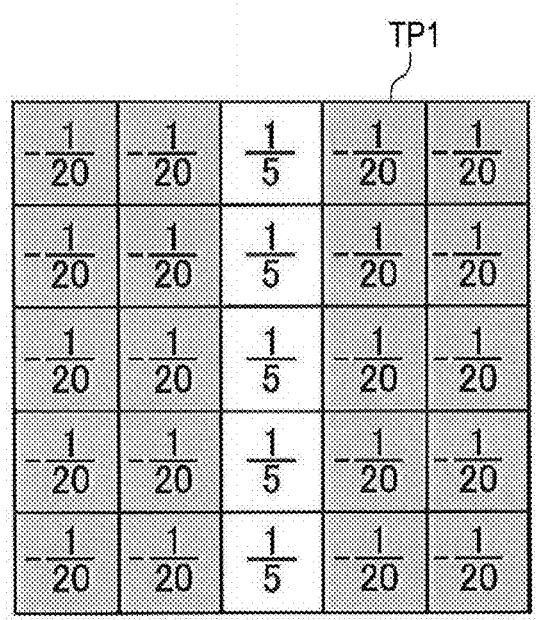
FIG. 4 is a view illustrating an example of a filter coefficient when the feature amount calculation unit illustrated in FIG. 2 uses a spatial filter.

FIG. 4 is a view illustrating an example of the filter coefficient when the template TP1 is used as the spatial filter. As illustrated in FIG. 4, the template TP1 has a shape in which a straight line extends in an upward-downward direction in the drawing. In FIG. 4, as an example, the template TP1 forms the spatial filter of 5×5 pixels. In this case, ⅕ is assigned as the filter coefficient to the pixels of the portion extending in the linear shape, and −1/20 is assigned as the filter coefficient to the other pixels. When a total value obtained by multiplying each of the filter coefficients by the image value of the corresponding pixel of the examination target area AR is calculated as the matching degree, in a case where all of the pixel values of the examination target area AR are values the same as each other, the matching degree is zero. On the other hand, when the examination target area AR includes an image of the blood vessel extending in a stripe streak in the upward-downward direction, the matching degree increases. As the value of the matching degree is greater, it can be described that the examination target area AR includes the image that approximates the template TP1. Therefore, the matching degree is calculated for each of the templates TP1 to TP4, and the highest matching degree having the greatest value in the calculated matching degrees is assigned to the central pixel of the examination target area AR, as the certainty of the blood vessel.

The feature amount calculation unit 222 determines whether or not the value of the certainty of the blood vessel in each pixel is greater than a predetermined value. When the value of the certainty of the blood vessel in the pixel is greater than the predetermined value, it is determined that the pixel is located in the blood vessel region. In this manner, the blood vessel region is extracted.

The image used by the feature amount calculation unit 222 to obtain the certainty of the blood vessel is not particularly limited as long as the blood vessel image appears. For example, in a case of the color image including the color components of red (R), green (G), and blue (B), a brightness image may be used, or an image of the red color component may be used. Alternatively, an image of a red chromaticity image having red chromaticity in which the degree of the red color component of each pixel is indicated as each pixel value by using the numerical value by a deviation angle θ illustrated in FIG. 7 (to be described later) may be used.

The representative value calculation unit 224 calculates a representative value (first representative evaluation value) of the certainty of the blood vessel of the biological tissue imaged by integrating the pixel evaluation value (first pixel evaluation value) relating to the certainty of the blood vessel of each pixel calculated by the feature amount calculation unit 222.

A process of integrating the pixel evaluation value (first pixel evaluation value) in each pixel may be an averaging process of calculating an average value of the pixel evaluation value (first pixel evaluation value) of each pixel, or other known processes, for example, a process of obtaining a median value may be used. The averaging process includes a process of obtaining a simple average value and a process of obtaining a weighted average value. In addition, as a known process, the following process may be used in which each pixel evaluation value (first pixel evaluation value) of the certainty of the blood vessel is divided into at least two or more ranked levels, and a total value P of the values obtained by multiplying the number of pixels belonging to each level by a predetermined weighting coefficient is substituted into a predetermined equation to calculate the representative value. In this case, for example, the predetermined equation is $1/(1+e^{-P})$. In this case, the weighting coefficient is preferably a coefficient obtained by multiple logistic regression analysis to have a correlation with a subjective evaluation result presented by a doctor.

Figure 5:
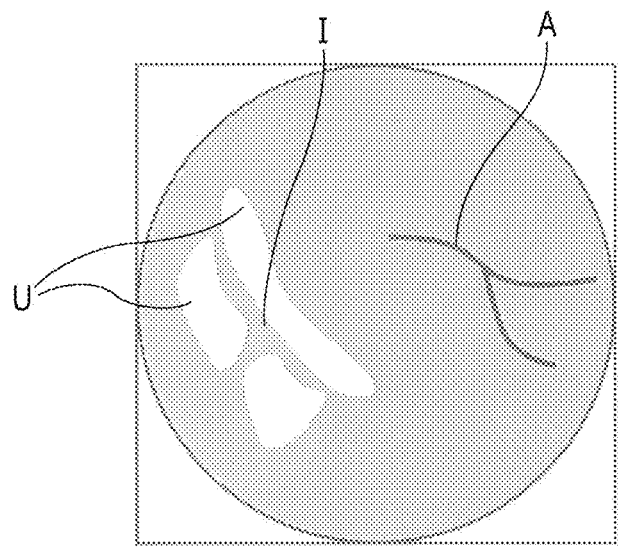
FIG. 5($a$) is a view schematically illustrating an example of an area where an ulcer and an inflammation occur, and FIG. 5($b$) is a view schematically illustrating an example of an evaluation result of a matching degree through a template used according to the embodiment.
Figure 5:
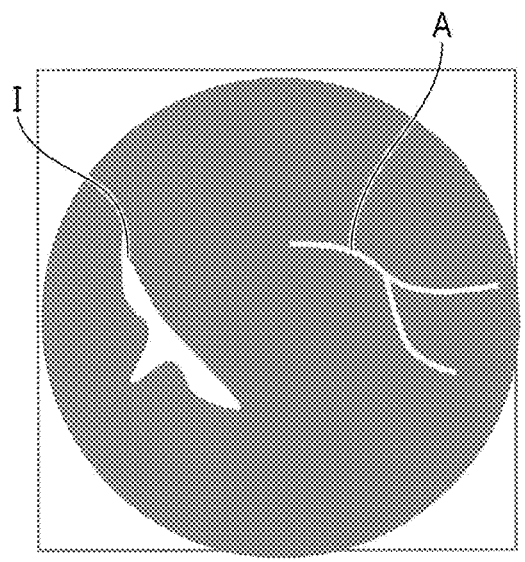

The representative value (first representative evaluation value) of the certainty of the blood vessel is the evaluation result of the matching degree obtained by the templates TP1 to TP4. The representative value (first representative evaluation value) of the certainty of the blood vessel includes a linear portion other than the blood vessel, as a region having a high matching degree obtained by the templates TP1 to TP4. For example, a strip-shaped and elongated inflamed area interposed between the two ulcer areas shows the high evaluation result of the certainty of the blood vessel (strip-shaped and elongated inflamed area is evaluated as a portion having high certainty of the blood vessel). FIG. 5(a) is a view schematically illustrating an example of an area where the ulcer and the inflammation appear, and FIG. 5(b) is a view schematically illustrating an example of a result in which the area is extracted as a blood vessel region from the evaluation result of the matching degree obtained by the templates TP1 to TP4. When there are a blood vessel image A and an inflamed area I extending in a strip shape between two ulcer areas U as illustrated in FIG. 5(a), the blood vessel image A and the inflamed area I are evaluated as the blood vessel region as illustrated in FIG. 5(b).

Therefore, in addition to the pixel evaluation value of the certainty of the blood vessel, the feature amount calculation unit 222 obtains the value in which the degree of the second feature that shares the line shape with the certainty of the blood vessel (first feature) and that is different from the first feature appearing in the attention area of the biological tissue which affects a level of the certainty of the blood vessel is converted into the numerical value, for each pixel. The representative value adjustment unit 226 evaluates the degree of the second feature by using the value indicating the degree of the second feature obtained for each pixel, and increases or decreases the representative value (first representative evaluation value) of the certainty of the blood vessel, based on the evaluation result of the degree of the second feature.

Specifically, as the degree of the second feature, paying attention to a fact that the degree of the red color component of the inflamed area I interposed between the two ulcer areas U becomes stronger as the degree of the ulcer becomes stronger, the feature amount calculation unit 222 calculates the red chromaticity indicating the high degree of the red color component, for each pixel. The red chromaticity is an example of the red color component, and is not limited to the red chromaticity described below as long as the degree including the red color component can be indicated by using the numerical value.

Figure 6:
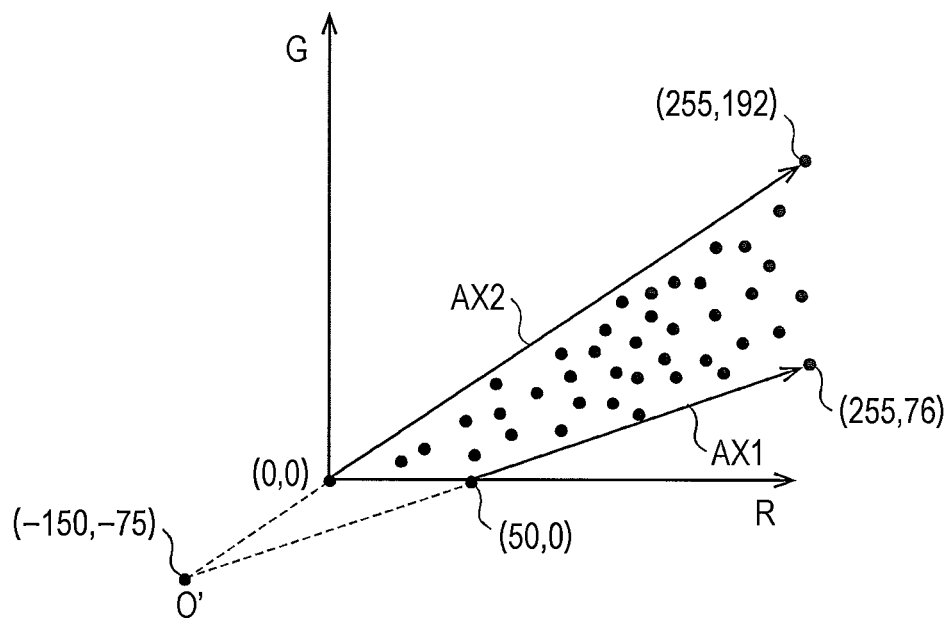
FIG. 6 is a view for describing red chromaticity calculated according to the embodiment.
Figure 7:
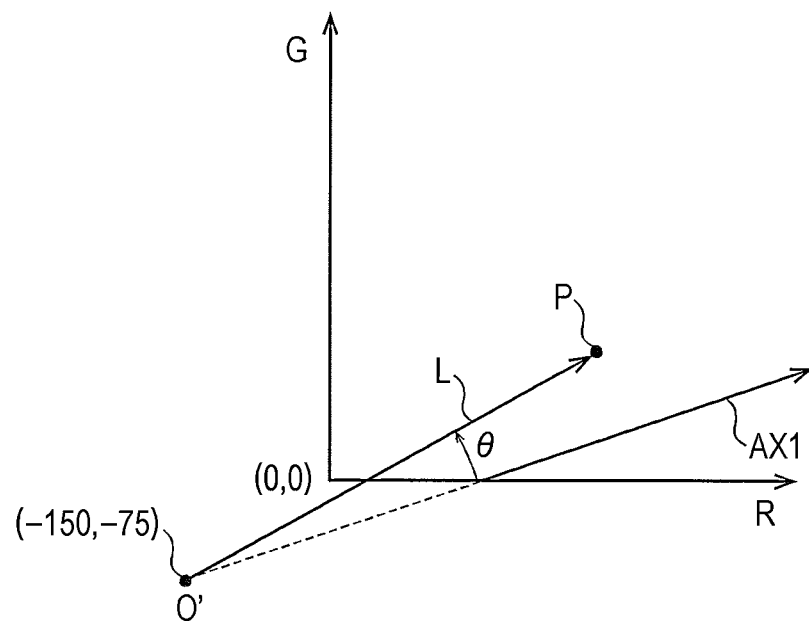
FIG. 7 is a view for describing the red chromaticity calculated according to the embodiment.

FIGS. 6 and 7 are views for describing the red chromaticity calculated according to the embodiment. FIG. 6 illustrates an example of the following result. In the color image of the biological tissue, the pixel value of the red color component and the pixel value of the green color component are subjected to preprocessing (color correction or tone adjustment). Thereafter, each pixel value is plotted on a coordinate system of an RG color space in which a horizontal axis represents values of the red color component and a vertical axis represents values of the green color component. The pixel value is expressed by an 8-bit value having a value from 0 to 255. As illustrated in FIG. 6, inside the RG color space, a straight line passing through (50, 0) and (255, 76) is set as one of reference axes, and a straight line passing through (0, 0) and (255, 192) is set as one of reference axes. For convenience of description, the former reference axis will be referred to as a "hemoglobin change axis AX1", and the latter reference axis will be referred to as a "mucosal change axis AX2".

The plot illustrated in FIG. 6 illustrates an example of the result obtained by analyzing a large number of reference images inside a body cavity. The reference images used in the analysis include examples of inflammation images in each stage such as examples of inflammation images showing the highest degree of the inflammation (examples of inflammation images showing the most severe level) and examples of inflammation images showing the lowest degree of inflammation (examples of images substantially considered as a healthy area).

As an area shows the strong inflammation, the red color component of the color components of the image is stronger than other components (green color component and blue color component). Therefore, an axis on a boundary line between a region where the plot is distributed and a region where the plot is not distributed, which is an axis on a boundary line closer to the horizontal axis than the vertical axis, for example, an axis on a boundary line passing through (50 and 0) and (255 and 76) in the example illustrated in FIG. 6 is set as an area showing the strongest degree of the inflammation, that is, an axis having a high correlation with the area showing the highest degree of the inflammation. The axis is the hemoglobin change axis AX1. The hemoglobin change axis AX1 is superimposed with the plot corresponding to the inflamed area showing the highest degree of the inflammation imaged under various imaging conditions, for example, lighting conditions of the illumination light. Therefore, the hemoglobin change axis AX1 is an axis to which plotted points converge as the degree of the inflammation of biological tissue becomes higher.

On the other hand, as an area is closer to the healthy area, the green color component (or the blue color component) of the color components of the image is stronger than the red color component. Therefore, the axis on the boundary line between the region where the plot is distributed and the region where the plot is not distributed, which is the axis on the boundary line closer to the vertical axis than the horizontal axis, for example, the axis on the boundary line passing through (0, 0) and (255, 192) in the example illustrated in FIG. 6 is set as an area showing the lowest degree of the inflammation, that is, an axis having a high correlation with an area considered as a substantially health area which is the area showing the lowest degree of the inflammation. The axis is the mucosal change axis AX2. The mucosal change axis AX2 is superimposed with the plot corresponding to the area showing the lowest degree of the inflammation imaged under various imaging conditions, for example, lighting conditions of the illumination light, that is, an area considered as a substantially normal area. Therefore, the mucosal change axis AX2 is the axis to which plotted pixel correspondence points converge as the degree of the inflammation becomes lower (closer to the healthy area).

Therefore, as the area is closer to the hemoglobin change axis AX1, the red color component becomes stronger, and as the area is closer to the mucosal change axis AX2, the red color component becomes weaker. Therefore, as illustrated in FIG. 7, the feature amount calculation unit 222 sets an intersection between the hemoglobin change axis AX1 and the mucosal change axis AX2 as a reference point O', and calculates the deviation angle θ at which an orientation of a line segment L connecting the reference point O' and a point P obtained by plotting the pixel value of each pixel deviates from the hemoglobin change axis AX1. In this manner, the feature amount calculation unit 222 normalizes the deviation angle θ so that the value is 255 when the deviation angle θ is zero and the value is zero when the deviation angle θ is $\theta_{MAX}$. The feature amount calculation unit 222 calculates the normalized deviation angle θ as the red chromaticity for each pixel. That is, with regard to each pixel, the feature amount calculation unit 222 obtains the red chromaticity falling within a range of 0 to 255 by performing a numerical processing for converting the degree of the red color into the numerical value, based on the information on the color component of each pixel.

The reference point O' is located at a coordinate (−150 and −75). An example in which the reference point O' is located at the coordinate (−150 and −75) has been described. However, the configuration is not limited thereto. The reference point O' can be changed as appropriate, and for example, may be an intersection between the horizontal axis and the vertical axis of the RG color space. In the above-described embodiment, the red chromaticity is determined by using the deviation angle θ on the RG color space. However, the deviation angle may be calculated on the RB color space, and may be determined by using the deviation angle.

In this way, the feature amount calculation unit 222 calculates the red chromaticity for each pixel from the image of the biological tissue.

The representative value adjustment unit 226 prepares a histogram of the red chromaticity by using the red chromaticity calculated by the feature amount calculation unit 222, and evaluates the degree of the ulcer by using at least one of a parameter of spread of the red chromaticity and the maximum value (maximum bin) of the red chromaticity.

Figure 8:
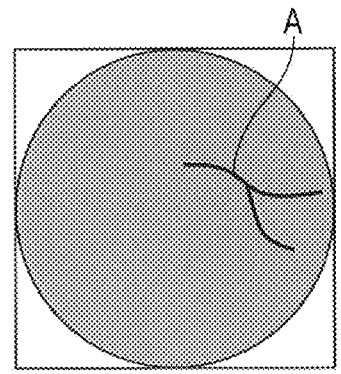
FIGS. 8(a) to 8(d) are views for describing a relationship between the red chromaticity and the ulcer.
Figure 8:
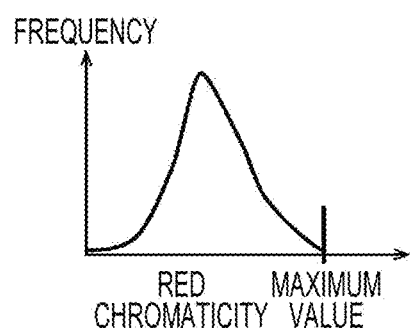
Figure 8:
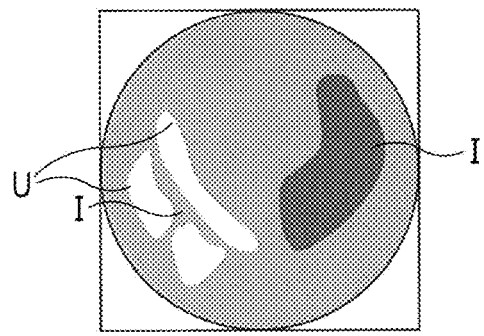
Figure 8:
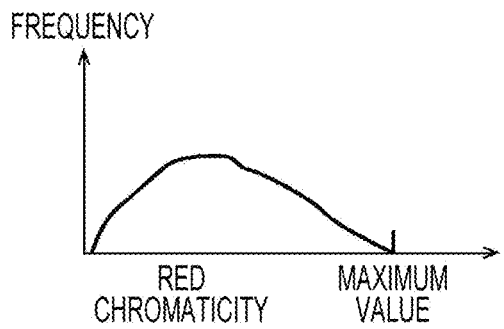

FIGS. 8(a) to 8(d) are views for describing a relationship between the red chromaticity and the ulcer. FIG. 8(a) is a view schematically illustrating an image having no ulcer and no inflammation although the blood vessel image A appears on the surface of a biological tissue. FIG. 8(b) is a view illustrating an example of the histogram of the result obtained by evaluating the red chromaticity for each pixel from the image illustrated in FIG. 8(a). In contrast, FIG. 8(c) is a view schematically illustrating an image in which the inflamed area I and the ulcer area U appear. FIG. 8(d) is a view illustrating an example of the histogram of the result obtained by evaluating the red chromaticity for each pixel from the image illustrated in FIG. 8(c).

As illustrated in FIGS. 8(b) and 8(d), when the inflamed area I appears, further the ulcer area U appears, and the degree of the lesion progresses, the distribution of the red chromaticity spreads, and the maximum value (maximum bin) becomes greater. That is, since the ulcer area U appears, the degree of the strip-shaped inflamed area I formed between the two ulcer areas U becomes stronger.

Figure 9:
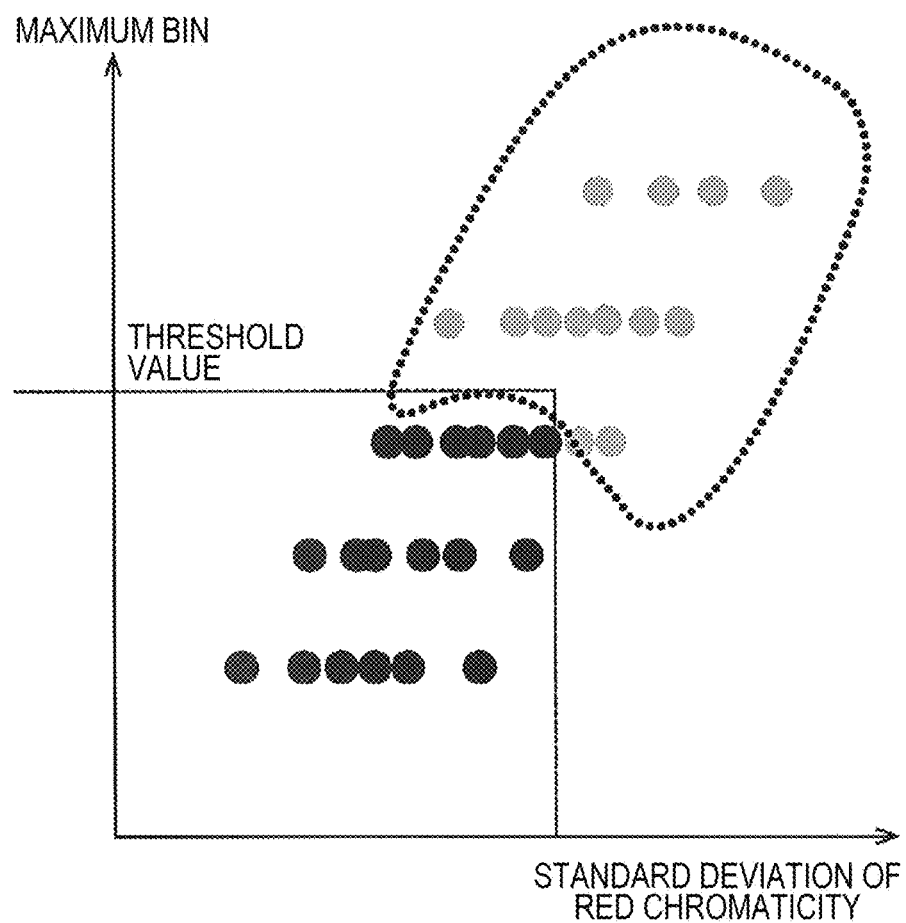
FIG. 9 is a view illustrating an example of a relationship between a standard deviation and a maximum bin of the red chromaticity.

FIG. 9 is a view illustrating an example of a relationship between a standard deviation the maximum bin of the red chromaticity. It can be understood that the maximum bin increases as the standard deviation of the red chromaticity increases. The maximum bin is a center value of a section in which a section value is maximized out of a plurality of sections having an equal interval which are used to sort sample data in the histogram. However, the maximum bin corresponds to the maximum value of the sample data, and the maximum value may be used instead of the maximum bin. Each of a plurality of dots illustrated in FIG. 9 shows an evaluation result of one image. The standard deviation of the red chromaticity is an example of the parameter of distribution spread in the histogram distribution relating to the value obtained by converting the red color component into the numerical value. Without being limited to the standard deviation, for example, a difference between the maximum value and the minimum value in the above-described distribution may be used.

Figure 10:
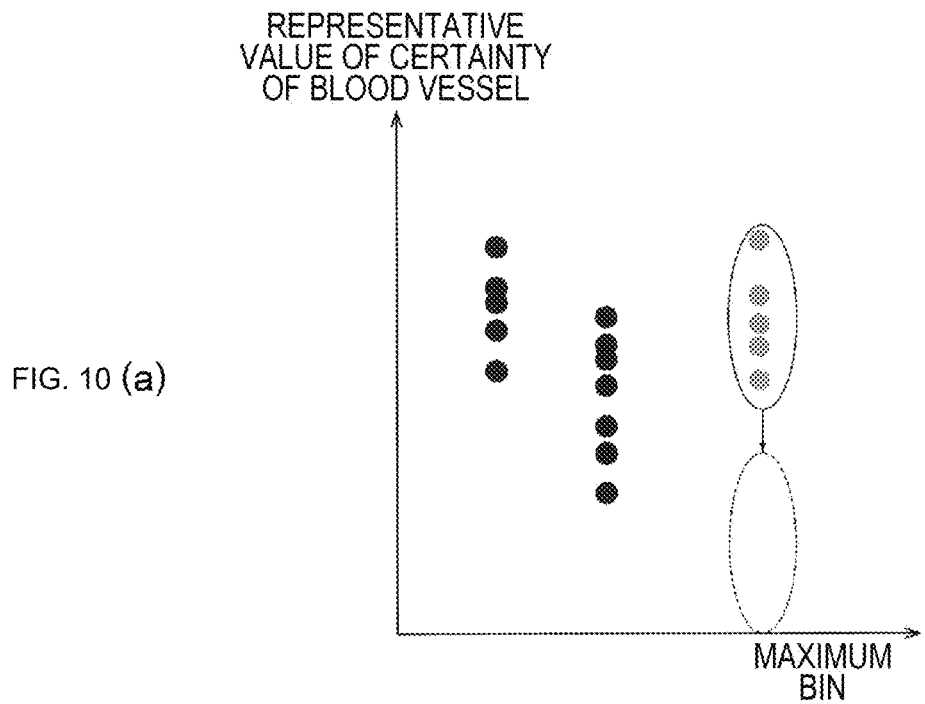
FIGS. 10(a) and 10(b) are views for describing an example of adjusting a representative value (first representative evaluation value) of the certainty of the blood vessel used according to the embodiment.
Figure 10:
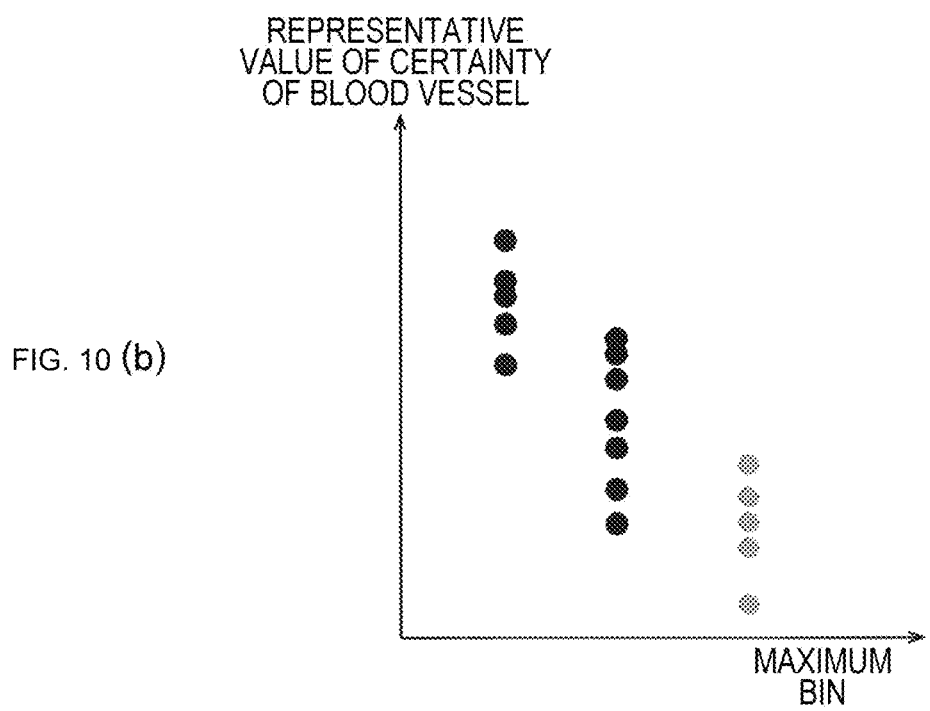

Therefore, the representative value adjustment unit 226 prepares the histogram of the red chromaticity, and increases or decreases the representative value (first representative evaluation value) of the certainty of the blood vessel, based on the degree of the ulcer evaluated by using at least one of the parameter of the spread of the red chromaticity and the maximum value (maximum bin) of the red chromaticity. For example, as illustrated in FIG. 9, when the maximum bin or the standard deviation of the red chromaticity exceeds a threshold value, the representative value adjustment unit 226 determines that the contribution of the degree of the ulcer cannot be ignored in the evaluation result of the certainty of the blood vessel, and Increases or decreases the representative value (first representative evaluation value) of the certainty of the blood vessel. FIGS. 10(a) and 10(b) are views for describing an example of adjusting the representative value (first representative evaluation value) of the certainty of the blood vessel which is used according to the embodiment. Each of a plurality of dots illustrated in FIGS. 10(a) and 10(b) shows the evaluation result of one image. As illustrated in FIG. 9(a), when the maximum bin exceeds the threshold value, the representative value adjustment unit 226 decreases the representative value of the certainty of the blood vessel as illustrated in FIG. 10(a), and adjusts the representative value of the certainty of the blood vessel as illustrated in FIG. 10(b). When the maximum bin or the standard deviation of the red chromaticity exceeds the threshold value, the representative value of the certainty of the blood vessel may be adjusted by decreasing the representative value of the certainty of the blood vessel with a constant decreasing amount regardless of the amount exceeding the predetermined threshold value. Alternatively, as the amount of the maximum bin or the standard deviation of the red chromaticity which exceeds the threshold value increases, the decreasing amount of the representative value of the certainty of the blood vessel may be increased.

As described above, the representative value adjustment unit 226 can adjust the certainty of the blood vessel in view of the evaluation result of the erroneously evaluated strip-shaped inflamed area which is included in the evaluation result of the certainty of the blood vessel. That is, the representative value adjustment unit 226 can use the numerical value to accurately evaluate the degree of the appearance feature appearing in the attention area of the biological tissue.

Figure 11:
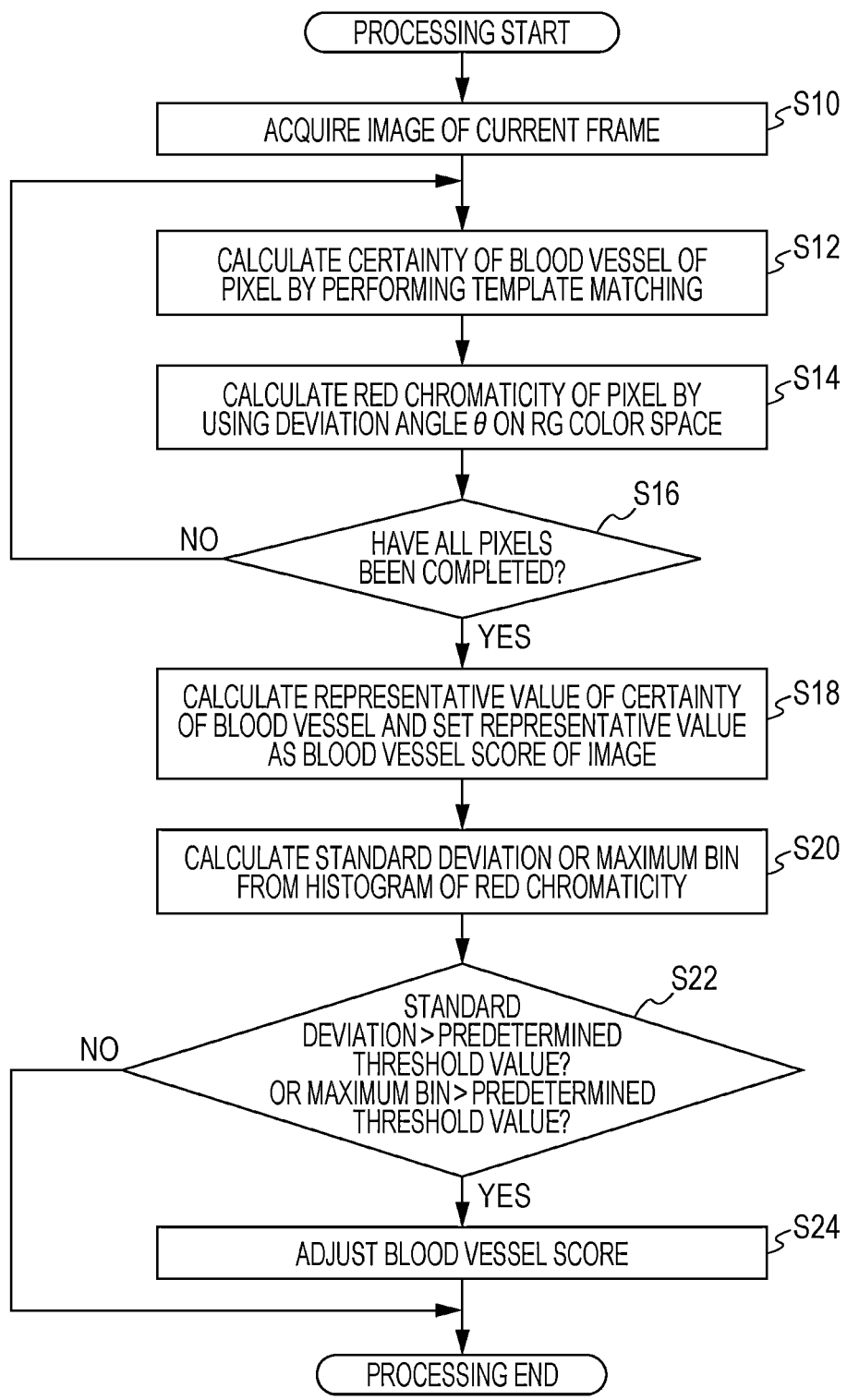
FIG. 11 is a view illustrating a processing flow for calculating a blood vessel score according to the embodiment.

FIG. 11 is a view illustrating a processing flow for calculating a blood vessel score which is the evaluation result of the certainty of a blood vessel by using an example of the certainty of a blood vessel as the first feature and an example of the ulcer as the second feature. The blood vessel score is a representative value of the above-described certainty of the blood vessel.

First, the image processing unit 220 acquires an image of a current frame (Step S10).

Next, the feature amount calculation unit 222 performs template matching using the plurality of templates TP1 to TP4 illustrated in FIG. 3, and calculates the numerical value of the certainty of the blood vessel in each pixel (Step S12).

In addition, the feature amount calculation unit 222 calculates the red chromaticity for each pixel by using the deviation angle θ on the RG color space illustrated in FIG. 7 (Step S14).

The feature amount calculation unit 222 determines whether or not the template matching and the red chromaticity calculation are performed on all pixels (Step S16). The template matching and the red chromaticity calculation are repeatedly performed until the template matching and the red chromaticity calculation are performed on all pixels.

When the determination in Step S16 is affirmative, the representative value calculation unit 224 calculates the representative value (first representative evaluation value) of the certainty of the blood vessel by integrating the certainty of the blood vessel which is calculated for each pixel, and sets the representative value as the blood vessel score (Step S18).

The representative value adjustment unit 226 calculates the standard deviation of the red chromaticity or the maximum bin (maximum value) of the red chromaticity from the histogram of the red chromaticity calculated by the feature amount calculation unit 222 for each pixel (Step S20).

Furthermore, the representative value adjustment unit 226 determines whether or not the standard deviation or the maximum bin of the red chromaticity exceeds a predetermined threshold value (Step S22). When the standard deviation or the maximum bin of the red chromaticity exceeds the predetermined threshold value, the blood vessel score determined in Step S18 is adjusted, based on the standard deviation or the maximum bin of red chromaticity (Step S24). When the standard deviation or the maximum bin of the red chromaticity does not exceed the predetermined threshold, the blood vessel score is not adjusted.

In this way, the blood vessel score indicating the certainty of the blood vessel can be accurately calculated.

The representative value adjustment unit 226 can adjust the certainty of the blood vessel in view of the evaluation result of the erroneously evaluated strip-shaped inflamed area included in the evaluation result of the certainty of the blood vessel. That is, the representative value adjustment unit 226 can use the numerical value to accurately evaluate the degree of the appearance feature appearing in the attention area of the biological tissue.

The blood vessel score can be used to evaluate severity indicating a degree of a lesion in a lesion area, and the evaluation result of the severity can be displayed on the monitor 300.

Figure 12:
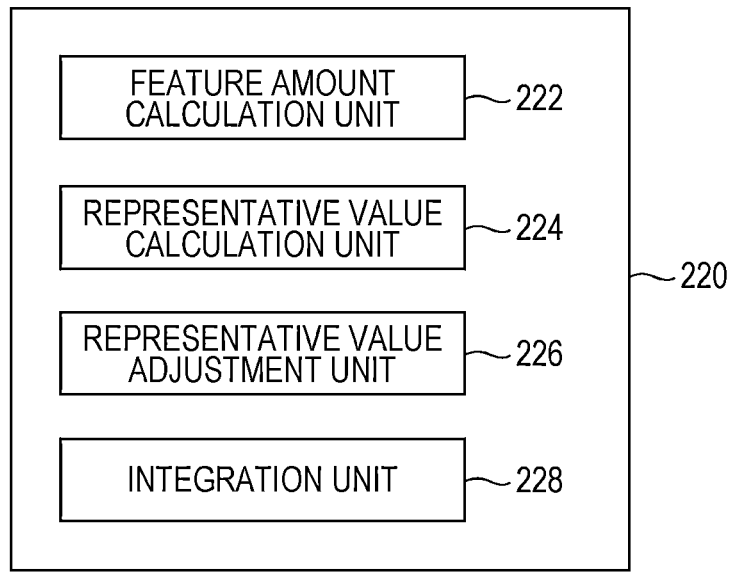
FIG. 12 is a view illustrating an example of a configuration of an image processing unit for calculating severity according to the embodiment.

FIG. 12 is a view illustrating an example of a configuration of the image processing unit 220 for calculating the severity.

The image processing unit 220 includes an integration unit 228 in addition to the feature amount calculation unit 222, the representative value calculation unit 224, and the representative value adjustment unit 226 which are illustrated in FIG. 2. Functions of the feature amount calculation unit 222, the representative value calculation unit 224, and the representative value adjustment unit 226 which are illustrated in FIG. 12 are the same as functions of the feature amount calculation unit 222, the representative value calculation unit 224, and the representative value adjustment unit 226 which are illustrated in FIG. 2, and thus, description of the functions will be omitted.

The severity is evaluated by the Integration unit 228. Specifically, the representative value calculation unit 224 calculates the representative value of the red chromaticity obtained by integrating the red chromaticity of each pixel in the whole image by using the red chromaticity of each pixel calculated in Step S14 illustrated in FIG. 11. The integrated red chromaticity is called the representative value of the red chromaticity of the biological tissue.

Furthermore, the integration unit 228 calculates a value of the severity by using the blood vessel score obtained in Step S18 and the representative value of the red chromaticity of the biological tissue. As an example, the severity is calculated by subtracting the blood vessel score from the representative value of the red chromaticity of the biological tissue. When the severity indicates the degree of the inflammation, as the degree of the inflammation becomes stronger, the representative value of the red chromaticity of the biological tissue becomes greater. In contrast, the image of the blood vessel is less likely to appear on the surface of the biological tissue, and the blood vessel score decreases. Therefore, in order to accurately indicate the severity of the inflammation by using the numerical value, the severity is calculated by subtracting the blood vessel score from the representative value of the red chromaticity of the biological tissue.

Furthermore, when the severity of the lesion becomes stronger in not only the inflammation but also the ulcer, the representative value of the red chromaticity of the biological tissue becomes greater. Moreover, the image of the blood vessel is likely to appear on the surface of the biological tissue, and the blood vessel score increases. Therefore, when the severity becomes stronger, the severity is calculated by adding the blood vessel score to the representative value of the red chromaticity of the biological tissue in order to accurately indicate the severity of the ulcer by using the numerical value.

When the lesion is the inflammation and when the lesion includes the inflammation and the ulcer, depending on whether or not the representative value of the red chromaticity of the biological tissue exceeds the threshold value, or depending on whether or not the blood vessel score exceeds the threshold value, it is preferable to select whether to perform a process of subtracting the blood vessel score from the representative value of the red chromaticity of the biological tissue or to perform a process of adding the blood vessel score to the representative value of the red chromaticity of the biological tissue. That is, when the representative value of the red chromaticity of the biological tissue exceeds the threshold value, or when the blood vessel score is smaller than the threshold value, it is preferable to select the process of adding the blood vessel score to the representative value of the red chromaticity of the biological tissue. When the representative value of the red chromaticity of the biological tissue is equal to or smaller than the threshold value, or when the blood vessel score is equal to or greater than the threshold value, it is preferable to select the process of subtracting the blood vessel score from the representative value of the red chromaticity of the biological tissue. In the adding process and the subtracting process, those in which the representative value of the red chromaticity of the biological tissue is multiplied by a predetermined coefficient and/or those in which the blood vessel score is multiplied by a predetermined coefficient may be used for the above-described adding process and subtracting process.

Figure 13:
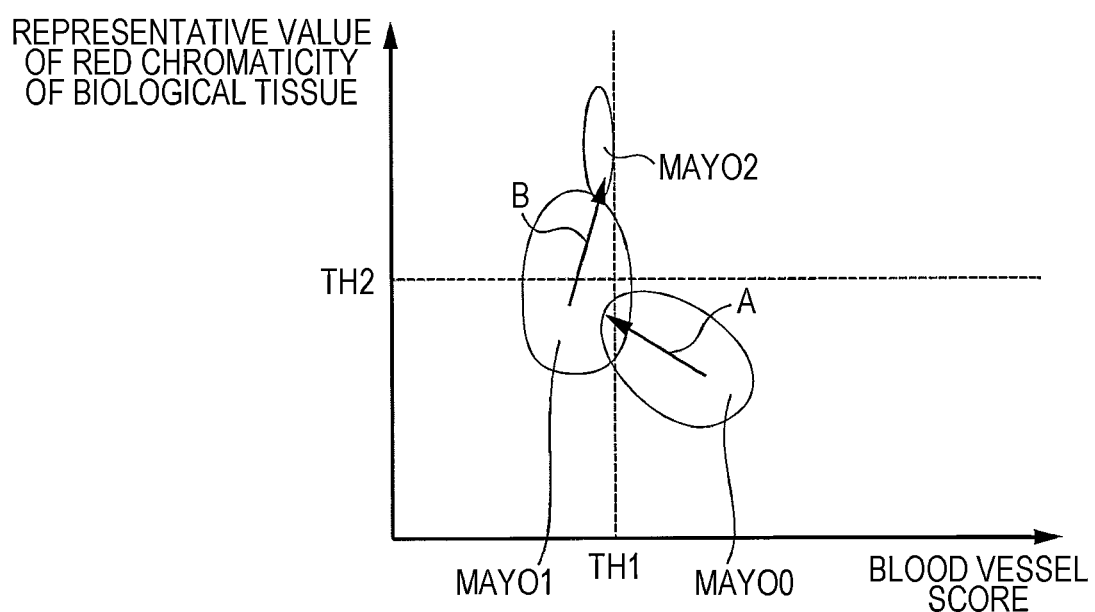
FIG. 13 is a view for describing an example in which an evaluation result of degrees of a first feature and a second feature which is obtained according to the embodiment varies in accordance with a progress of a degree of a lesion.

FIG. 13 is a view for describing an example in which the evaluation result of the degrees of the first feature and the second feature according to the embodiment varies in accordance with a progress of the degree of the lesion. In FIG. 13, in a coordinate system in which the horizontal axis represents the blood vessel score and the vertical axis represents the representative value of the red chromaticity of the biological tissue, the evaluation result obtained by using an image example of a lesion area of an ulcerative colitis shows a direction of moving in accordance with the progress of the degree of the lesion. MAYO illustrated in FIG. 13 shows a value of MAYO endoscopic subscore which is a subjective evaluation result of a doctor, and shows that the degree of the lesion becomes stronger as MAYO0, MAYO1, and MAYO2 progress. As illustrated in FIG. 13, as the degree of the lesion becomes stronger in a section of MAYO0 to MAYO1 (region A where the inflammation mainly appears), the representative value of the red chromaticity of the biological tissue becomes greater, and the representative value of the blood vessel score becomes smaller. As the degree of the lesion becomes stronger in a section of MAYO1 to MAYO2 (region B where the ulcer mainly appears), the representative value of the red chromaticity of the biological tissue becomes greater, and the representative value of the blood vessel score also becomes greater. Therefore, even when the representative values of the red chromaticity of the biological tissue happens to be the same as each other, a level of the severity can be evaluated by a difference in the blood vessel scores. Similarly, even when the blood vessel scores happen to be the same as each other, a level of the severity can be evaluated by a difference in the representative values of the red chromaticity of the biological tissue.

In this way, from a viewpoint of a fact that the severity of the lesion area can be accurately evaluated, it is desirable that the blood vessel score used in evaluating the severity of the lesion area can be accurately evaluated.

In the above-described embodiment, the first pixel evaluation value is the value obtained by converting the degree of the certainty relating to the shape into the numerical value as the degree of the first feature, and the evaluation result of the degree of the second feature is the evaluation result relating to the color component in the image. Accordingly, the first feature can be accurately evaluated separately from the second feature.

The degree of the second feature is the degree of the ulcer of the biological tissue. The feature amount calculation unit 222 evaluates the degree of the second feature by using at least one of the standard deviation (spread information) in the histogram distribution relating to the red chromaticity obtained by converting the red color component for each pixel of the image into the numerical value and the maximum value of the red chromaticity of the pixel in the image. Accordingly, it is possible to obtain an accurate evaluation result of the certainty of the blood vessel.

In addition, as the severity of the lesion, the integration unit 228 is configured to calculate one numerical value obtained by calculating and integrating the blood vessel score (first representative evaluation value) adjusted by the representative value adjustment unit 226 and the representative value of the red chromaticity of the biological tissue which is calculated by the representative value calculation unit 224. Accordingly, the severity can be accurately calculated by using the blood vessel score which is an accurate evaluation result adjusted by the representative value adjustment unit 226.

Figure 14:
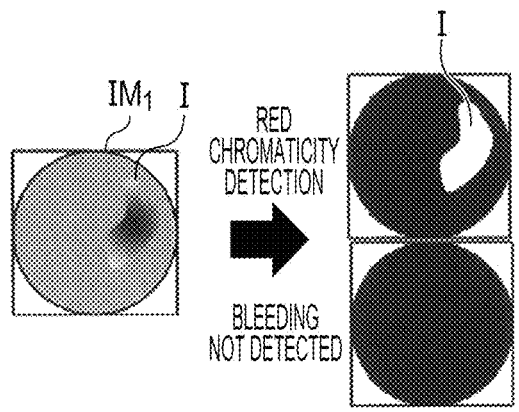
FIGS. 14(a) to 14(c) are views for describing an example of an evaluation result obtained according to the embodiment.
Figure 14:
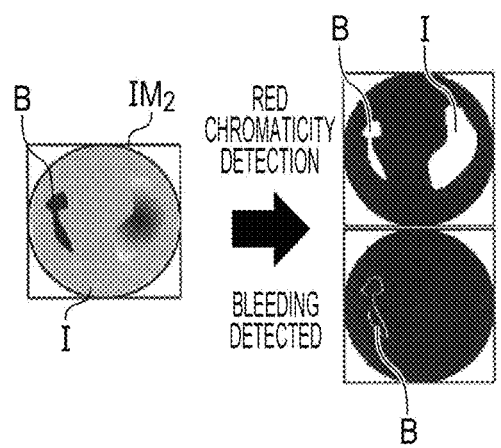
Figure 14:
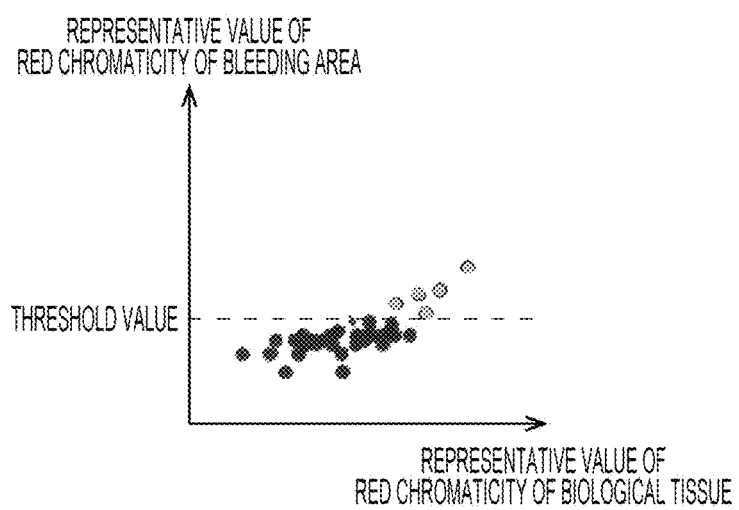

In the above-described embodiment, with regard to the operation of the image processing unit 220, the degree of the first feature is the degree of the certainty of the blood vessel, and the degree of the second feature is the degree of the ulcer. An embodiment described below adopts a form as follows. The degree of the first feature is the degree of the inflammation. The degree of the inflammation is a value obtained by converting the degree of the color component into the numerical value. The degree of the second feature is a degree of bleeding. The degree of the bleeding is a value in which the degree of the color component is converted into the numerical value. FIGS. 14(a) to 14(c) are views for describing an example of the evaluation result in which the degree of the first feature and the degree of the second feature are converted into the numerical value by using the degree of the color component.

In addition to the inflamed area which becomes red due to the inflammation, the biological tissue also has a bleeding area in which the surface of the biological tissue becomes red after the mucous is thinned and bleeds due to the inflammation. That is, in some cases, the degree of the first feature is set as the degree of the inflammation in the inflamed area so that the evaluation using the numerical value is performed by using the degree of the red color component. In this case, the evaluation result obtained by converting the degree of the red color component into the numerical value also includes the evaluation result of the red color component of the bleeding area which shows a strong red color.

That is, the feature amount calculation unit 222 obtains the red chromaticity of each pixel showing the degree of the red color component appearing in the inflamed area, based on the above-described deviation angle θ, for each pixel. The representative value calculation unit 224 obtains the representative value of the red chromaticity of the biological tissue which is the representative evaluation value of the first feature by integrating the red chromaticity obtained for each pixel.

However, the evaluation result also includes the evaluation result of the bleeding area. The bleeding area is an area where the blood bleeds and covers the surface of the biological tissue, and a boundary with the area not covered with the blood appears as an edge. Therefore, the representative value adjustment unit 226 specifies the bleeding area by using a known edge detection technique.

As illustrated in FIG. 14(a), when an image $IM_1$ of the biological tissue has an inflamed area I, a region of the inflamed area I can be evaluated separately from a non-inflamed area by using the red chromaticity. On the other hand, since the image $IM_1$ does not have the bleeding area, the edge which is the boundary between the bleeding area and the non-bleeding area is not detected by using the edge detection technique, and it is evaluated that the bleeding area does not exist.

In contrast, as illustrated in FIG. 14(b), when an image $IM_2$ of the biological tissue has the inflamed area I and a bleeding area B, regions of the inflamed area I and the bleeding area B can be evaluated by using the red chromaticity. However, in this case, the evaluation result of the red chromaticity includes the bleeding area B. Accordingly, in order to accurately evaluate the degree of the inflammation in this area, it is necessary to reduce the contribution of the bleeding area B to the evaluation result.

Therefore, the representative value adjustment unit 226 can extract an edge that defines a range of the bleeding area B by using the known edge detection technique. Furthermore, the representative value of the red chromaticity in the range of the bleeding area B defined from the extracted edge is obtained. In this manner, the red chromaticity of the biological tissue is adjusted by increasing or decreasing the representative value of the red chromaticity of the biological tissue obtained by the representative value calculation unit 224, based on the representative value of the red chromaticity of the bleeding area. The representative value of the red chromaticity of the bleeding area may be an average value of the red chromaticity. However, in view of the spread of the bleeding area, the representative value may be an integrated value of the red chromaticity of the bleeding area, or may be a value obtained by multiplying the average value of the red chromaticity by a coefficient determined according to the spread of the bleeding area.

FIG. 14(c) illustrates an example of a scatter diagram of a plurality of evaluation results in which the horizontal axis represents the representative value of the red chromaticity of the biological tissue and the vertical axis represents the representative value of the red chromaticity of the bleeding area. In FIG. 14(c), when the representative value of the red chromaticity of the bleeding area exceeds a predetermined threshold value (gray plot in FIG. 14(c)), it is not possible to ignore a degree in which the red chromaticity of the bleeding area is included in the representative value of the red chromaticity of the biological tissue. Accordingly, it is preferable to adjust the representative value of the red chromaticity of the biological tissue by increasing or decreasing the representative value of the red chromaticity of the biological tissue, based on the representative value of red chromaticity of the bleeding area. In this case, with regard to the amount to be adjusted, it is preferable to increase a decreasing amount for decreasing the representative value of the red chromaticity of the biological tissue, as a larger amount of the representative value of the red chromaticity of the bleeding area exceeds the threshold value.

In this way, the representative value of the red chromaticity of the biological tissue is increased or decreased, based on the representative value of the red chromaticity of the bleeding area. Accordingly, the degree of the inflammation in the inflamed area can be accurately evaluated.

The pixel evaluation value calculated by the image processing unit 220 is the value obtained by converting the degree of the red chromaticity into the numerical value as the degree of the inflammation. Furthermore, the evaluation result of the degree of bleeding which is obtained by the image processing unit 220 is the evaluation result of the degree of the red chromaticity of the bleeding area. Therefore, the red chromaticity serving as an index of the degree of the inflammation and the red chromaticity serving as an index of the degree of the bleeding relate to the same red color component that determines the pixel value of the image. However, the evaluation result of the degree of the bleeding is the red chromaticity in a region surrounded by the edge extracted by using the known edge detection technique by using a fact that the boundary between the bleeding area and the non-bleeding area appears as an edge (second shape). Therefore, the inflamed area can be accurately evaluated by using the adjusted red chromaticity of the biological tissue.

In the embodiment illustrated in FIGS. 14(a) to 14(c), the degree of the first feature is the degree of the inflamed area, the degree of the inflammation of the inflamed area is evaluated by using the degree of the red color component of the biological tissue, the degree of the second feature is the degree of the bleeding in a region where the surface of the biological tissue is covered with the blood due to the bleeding of the biological tissue, and the degree of the bleeding is a value obtained by converting the degree including the red color component into the numerical value in the region covered with the blood due to the bleeding.

In this way, the representative value adjustment unit 226 can adjust the degree of the inflammation in the inflamed area in view of the evaluation result of the red chromaticity of the erroneously evaluated bleeding area included in the representative value of the red chromaticity of the biological tissue which is calculated for evaluating the degree of the inflammation of the inflamed area. That is, the representative value adjustment unit 226 can use the numerical value to accurately evaluate the degree of the appearance feature appearing in the attention area of the biological tissue.

Hitherto, the endoscope system of the present invention has been described in detail. The present invention is not limited to the above-described embodiments and examples. As a matter of course, various improvements or modifications may be made within the scope not departing from the concept of the present invention.

REFERENCE SIGNS LIST

1 endoscope system
100 electronic scope
200 processor for electronic endoscope
202 system controller
204 memory
206 timing controller
208 operation panel
220 image processing unit
222 feature amount calculation unit
224 representative value calculation unit
226 representative value adjustment unit
228 integration unit
230 light source unit
300 monitor
400 printer
600 server

The invention claimed is:
1. An endoscope system comprising:
an electronic endoscope configured to image a biological tissue;
a processor including an image processing unit configured to use a numerical value to evaluate a degree of an appearance feature appearing in an attention area of the biological tissue by using an image of the attention area of the biological tissue imaged by the electronic endoscope; and
a monitor configured to display information on the numerical value,
wherein the image processing unit includes
a feature amount calculation unit configured to calculate a first pixel evaluation value featured by a first color component or a first shape appearing as a first feature in the attention area, the first pixel evaluation value indicating a degree of the first feature which relates to the first color component or the first shape indicated by the attention area, for each pixel from the image, a representative value calculation unit configured to calculate a first representative evaluation value relating to the first feature of the imaged biological tissue by integrating the first pixel evaluation value of each pixel in the image, and a representative value adjustment unit configured to evaluate a degree of a second feature that shares the first color component or the first shape with the first feature and that appears in the attention area of the biological tissue which affects a level of the first pixel evaluation value by using at least one of a second color component and a second shape of the attention area, and to increase or decrease the first representative evaluation value, based on an evaluation result of a degree of the second feature.

2. The endoscope system according to claim 1, wherein the representative value adjustment unit is configured to evaluate a degree of a third feature that shares the first color component or the first shape with the first feature and that appears in the attention area which affects a level of the first pixel evaluation value by using at least one of a third color component and a third shape of the attention area, and to increase or decrease the first representative evaluation value, based on an evaluation result of a degree of the second feature and an evaluation result of a degree of the third feature.

3. The endoscope system according to claim 1, wherein the first pixel evaluation value is a value obtained by converting a degree of certainty relating to the first shape into a numerical value, as a degree of the first feature, and the evaluation result of a degree of the second feature is an evaluation result relating to the second color component in the image.

4. The endoscope system according to claim 3, wherein a degree of the first feature is certainty of a linearly extending blood vessel in a blood vessel appearing on a surface of the biological tissue a degree of the second feature is a degree of an ulcer of the biological tissue, and the representative value adjustment unit is configured to evaluate the degree of the second feature by using at least one of a parameter of a distribution spread in a histogram distribution relating to values obtained by converting a red color component for each pixel of the image into a numerical value, and a maximum value out of the values obtained by converting the red color component into the numerical value.

5. The endoscope system according to claim 1, wherein the first pixel evaluation value is a value obtained by converting a degree of the first color component into a numerical value as a degree of the first feature, the evaluation result of a degree of the second feature is an evaluation result of a degree including the second color component in a region where an appearing range of the second feature is extracted as the second shape, and the second color component and the first color component are the same pixel color components which determine a pixel value of the image.

6. The endoscope system according to claim 5, wherein a degree of the first feature is a degree of an inflammation of an inflamed area in the attention area, and the degree of the inflammation is evaluated by a degree of a red color component of the image, and a degree of the second feature is a degree of bleeding in a region where a surface of the biological tissue is covered with blood due to bleeding of the biological tissue, and the degree of the bleeding is a value obtained by converting a degree including the red color component in the region into a numerical value.

7. The endoscope system according to claim 1, wherein the image processing unit is configured to obtain severity of a lesion in which a degree of the lesion of the biological tissue is expressed as one value by using at least information on a color component of the image, from the image of the biological tissue which is obtained by the electronic endoscope, the feature amount calculation unit is configured to calculate a plurality of pixel evaluation values corresponding to a plurality of appearance features, in which each of the plurality of appearance features appearing in the lesion area is featured by a color component indicated by the lesion area or a shape of the lesion area, the plurality of pixel evaluation values indicating each degree of the plurality of features relating to the color component indicated by the lesion area or the shape of the lesion area, for each pixel from the image, the plurality of pixel evaluation values include the first pixel evaluation value, the representative value calculation unit is configured to calculate the plurality of representative evaluation values including the first representative evaluation value of the biological tissue imaged by integrating each of the plurality of pixel evaluation values including the first pixel evaluation value of each pixel in the image for each of the plurality of appearance features, and the image processing unit includes an integration unit configured to calculate one numerical value obtained by calculating and integrating at least two representative evaluation values including the first representative evaluation value adjusted by the representative value adjustment unit out of the plurality of representative evaluation values, as severity of the lesion.

* * * * *